(12) United States Patent
Mookkan et al.

(10) Patent No.: US 8,992,929 B2
(45) Date of Patent: Mar. 31, 2015

(54) MONOCLONAL ANTIBODY SPECIFIC TO MAJOR NEUTRALIZING EPITOPE OF INFLUENZA H5 HEMAGGLUTININ

(75) Inventors: Prabakaran Mookkan, Singapore (SG); Fang He, Singapore (SG); Hwei-Sing Jimmy Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 89 days.

(21) Appl. No.: 13/817,892

(22) PCT Filed: Aug. 23, 2010

(86) PCT No.: PCT/SG2010/000306
§ 371 (c)(1),
(2), (4) Date: Apr. 24, 2013

(87) PCT Pub. No.: WO2012/026878
PCT Pub. Date: Mar. 1, 2012

(65) Prior Publication Data
US 2013/0202608 A1    Aug. 8, 2013

(51) Int. Cl.
| | | |
|---|---|---|
| A61K 39/145 | (2006.01) | |
| A61K 39/42 | (2006.01) | |
| C12N 5/12 | (2006.01) | |
| C07K 16/10 | (2006.01) | |
| A61K 39/00 | (2006.01) | |

(52) U.S. Cl.
CPC ....... C07K 16/1018 (2013.01); *A61K 2039/505* (2013.01); *C07K 2317/24* (2013.01); *C07K 2317/34* (2013.01); *C07K 2317/76* (2013.01)
USPC .................. 424/159.1; 424/139.1; 435/320.1; 435/339; 530/388.3

(58) Field of Classification Search
None
See application file for complete search history.

(56) References Cited

U.S. PATENT DOCUMENTS

2009/0068637 A1    3/2009    Xia et al.

FOREIGN PATENT DOCUMENTS

EP    2 174 957 A1    4/2010

OTHER PUBLICATIONS

Prabakaran et al. Combination therapy using chimeric monoclonal antibodies protects mice from lethal H5N1 infection and prevents formation of escape mutants. PLoS One. May 22, 2009;4(5):e5672.*
Ohno et al. Antigen-binding specificities of antibodies are primarily determined by seven residues of VH. Proc Natl Acad Sci U S A. May 1985;82(9):2945-9.*
Database EMBL [Online], "*Mus musculus domesticus* anti-H5 hemagglutinin specific immunoglobulin light chain variable region mRNA, partial cds," Nov. 2, 2010, XP002717480, retrieved from EBI accession No. EMBL: HM448828, 1 page.
Database EMBL [Online], "*Mus musculus domesticus* anti-H5 hemagglutinin specific immunoglobulin heavy chain variable region mRNA, partial cds," Nov. 2, 2010, XP002717481, retrieved from EBI accession No. EMBL: HM448827, 1 page.
Kostolansky, F. et al., "The strong positive correlation between effective affinity and infectivity neutralization of highly cross-reactive monoclonal antibody IIB4, which recognizes antigenic site B on influenza A virus haemagglutinin," Journal of General Virology, Jul. 1, 2000, pp. 1727-1735.
Mookkan, P. et al., "Combination Therapy Using Chimeric Monoclonal Antibodies Protects Mice from Lethal H5N1 Infection and Prevents Formation of Escape Mutants," PLoS ONE, vol. 4, Issue 5, May 22, 2009, e5672, pp. 1-10.

* cited by examiner

*Primary Examiner* — Zachariah Lucas
*Assistant Examiner* — Nick Zou
(74) *Attorney, Agent, or Firm* — Rothwell, Figg, Ernst & Manbeck P.C.

(57) ABSTRACT

The present invention relates to the murine monoclonal antibody 4C2 or to chimeric or humanized monoclonal antibodies specific to a major neutralizing epitope of influenza H5 hemagglutinin and active fragments thereof. The present invention also relates to methods and compositions for the prophylaxis and treatment of H5N1 influenza using such murine or chimeric or humanized monoclonal antibodies or fragments thereof.

23 Claims, 8 Drawing Sheets

SEQUENCE LISTING

<160> NUMBER OF SEQ ID NOS: 24

<210> SEQ ID NO 1
<211> LENGTH: 300
<212> TYPE: DNA
<213> ORGANISM: Mus musculus
<220> FEATURE:
<221> NAME/KEY: CDS
<222> LOCATION: (1)..(300)
<220> FEATURE:
<221> NAME/KEY: misc_feature
<222> LOCATION: (70)..(87)
<223> OTHER INFORMATION: Light variable chain CDR1
<220> FEATURE:
<221> NAME/KEY: misc_feature
<222> LOCATION: (139)..(147)
<223> OTHER INFORMATION: Light variable chain CDR2
<220> FEATURE:
<221> NAME/KEY: misc_feature
<222> LOCATION: (256)..(282)
<223> OTHER INFORMATION: Light variable chain CDR3

<400> SEQUENCE: 1

```
atg acg cag tct cca tcc tcc atg tct gta tct ctg gga gac aca gtc      48
Met Thr Gln Ser Pro Ser Ser Met Ser Val Ser Leu Gly Asp Thr Val
1               5                   10                  15 agc atc act tgc cat gca agt cag gac att agt ggt cat ata ggg tgg      96
Ser Ile Thr Cys His Ala Ser Gln Asp Ile Ser Gly His Ile Gly Trp
                20                  25                  30 ttg cag cag aaa cca ggg aaa tca ttt aag ggc ctg atc tat cat gga     144
Leu Gln Gln Lys Pro Gly Lys Ser Phe Lys Gly Leu Ile Tyr His Gly
            35                  40                  45 acc aac ttg gaa gat gga gtt cca tca agg ttc agt ggc agt gga tct     192
Thr Asn Leu Glu Asp Gly Val Pro Ser Arg Phe Ser Gly Ser Gly Ser
        50                  55                  60 gga gca gat ttt tct ctc acc atc agc agc ctg gaa tct gaa gat ttt     240
Gly Ala Asp Phe Ser Leu Thr Ile Ser Ser Leu Glu Ser Glu Asp Phe
65                  70                  75                  80 gca gac tat tac tgt gta cag tat gtt cag ttt ccg tgg acg ttc ggt     288
Ala Asp Tyr Tyr Cys Val Gln Tyr Val Gln Phe Pro Trp Thr Phe Gly
                85                  90                  95 gga ggc acc aag                                                     300
Gly Gly Thr Lys
            100
```

<210> SEQ ID NO 2
<211> LENGTH: 100
<212> TYPE: PRT
<213> ORGANISM: Mus musculus

<400> SEQUENCE: 2

```
Met Thr Gln Ser Pro Ser Ser Met Ser Val Ser Leu Gly Asp Thr Val
1               5                   10                  15

Ser Ile Thr Cys His Ala Ser Gln Asp Ile Ser Gly His Ile Gly Trp
                20                  25                  30

Leu Gln Gln Lys Pro Gly Lys Ser Phe Lys Gly Leu Ile Tyr His Gly
            35                  40                  45

Thr Asn Leu Glu Asp Gly Val Pro Ser Arg Phe Ser Gly Ser Gly Ser
        50                  55                  60

Gly Ala Asp Phe Ser Leu Thr Ile Ser Ser Leu Glu Ser Glu Asp Phe
65                  70                  75                  80

Ala Asp Tyr Tyr Cys Val Gln Tyr Val Gln Phe Pro Trp Thr Phe Gly
                85                  90                  95
```

Gly Gly Thr Lys
        100

<210> SEQ ID NO 3
<211> LENGTH: 325
<212> TYPE: DNA
<213> ORGANISM: Mus musculus
<220> FEATURE:
<221> NAME/KEY: CDS
<222> LOCATION: (1)..(324)
<220> FEATURE:
<221> NAME/KEY: misc_feature
<222> LOCATION: (64)..(87)
<223> OTHER INFORMATION: Heavy variable chain CDR1
<220> FEATURE:
<221> NAME/KEY: misc_feature
<222> LOCATION: (139)..(162)
<223> OTHER INFORMATION: Heavy variable chain CDR2
<220> FEATURE:
<221> NAME/KEY: misc_feature
<222> LOCATION: (277)..(312)
<223> OTHER INFORMATION: Heavy variable chain CDR3

<400> SEQUENCE: 3

```
cag gag tct ggg gct gag ctg gtg agg cct ggg gct tca gtg aag ctg      48
Gln Glu Ser Gly Ala Glu Leu Val Arg Pro Gly Ala Ser Val Lys Leu
1               5                   10                  15 tcc tgc aag gat tct ggc tac acg ttc acc acc tac tgg atg aac tgg      96
Ser Cys Lys Asp Ser Gly Tyr Thr Phe Thr Thr Tyr Trp Met Asn Trp
            20                  25                  30 gtt aag cag agg cct gag caa ggc ctt gag tgg att gga agg att gat     144
Val Lys Gln Arg Pro Glu Gln Gly Leu Glu Trp Ile Gly Arg Ile Asp
        35                  40                  45 cct tac gat agt gaa act cac tac aat caa aag ttc aag gac aag gcc     192
Pro Tyr Asp Ser Glu Thr His Tyr Asn Gln Lys Phe Lys Asp Lys Ala
    50                  55                  60 ata ttg act gta gac aaa tcc tcc aac aca gcc tac atg caa ctc agc     240
Ile Leu Thr Val Asp Lys Ser Ser Asn Thr Ala Tyr Met Gln Leu Ser
65                  70                  75                  80 agc ctg aca tct gag gac tct gcg gtc tat tac tgt gta agg gga ggg     288
Ser Leu Thr Ser Glu Asp Ser Ala Val Tyr Tyr Cys Val Arg Gly Gly
                85                  90                  95 tct acg gtc gcc tac ttc ggt gtc tgg ggc caa ggg a                   325
Ser Thr Val Ala Tyr Phe Gly Val Trp Gly Gln Gly
            100                 105
```

<210> SEQ ID NO 4
<211> LENGTH: 108
<212> TYPE: PRT
<213> ORGANISM: Mus musculus

<400> SEQUENCE: 4

Gln Glu Ser Gly Ala Glu Leu Val Arg Pro Gly Ala Ser Val Lys Leu
1               5                   10                  15

Ser Cys Lys Asp Ser Gly Tyr Thr Phe Thr Thr Tyr Trp Met Asn Trp
            20                  25                  30

Val Lys Gln Arg Pro Glu Gln Gly Leu Glu Trp Ile Gly Arg Ile Asp
        35                  40                  45

Pro Tyr Asp Ser Glu Thr His Tyr Asn Gln Lys Phe Lys Asp Lys Ala
    50                  55                  60

Ile Leu Thr Val Asp Lys Ser Ser Asn Thr Ala Tyr Met Gln Leu Ser
65                  70                  75                  80

Ser Leu Thr Ser Glu Asp Ser Ala Val Tyr Tyr Cys Val Arg Gly Gly
                85                  90                  95

Ser Thr Val Ala Tyr Phe Gly Val Trp Gly Gln Gly
            100                 105

<210> SEQ ID NO 5
<211> LENGTH: 6
<212> TYPE: PRT
<213> ORGANISM: Mus musculus

<400> SEQUENCE: 5

Gln Asp Ile Ser Gly His
1               5

<210> SEQ ID NO 6
<211> LENGTH: 3
<212> TYPE: PRT
<213> ORGANISM: Mus musculus

<400> SEQUENCE: 6

His Gly Thr
1

<210> SEQ ID NO 7
<211> LENGTH: 9
<212> TYPE: PRT
<213> ORGANISM: Mus musculus

<400> SEQUENCE: 7

Val Gln Tyr Val Gln Phe Pro Trp Thr
1               5

<210> SEQ ID NO 8
<211> LENGTH: 8
<212> TYPE: PRT
<213> ORGANISM: Mus musculus

<400> SEQUENCE: 8

Gly Tyr Thr Phe Thr Thr Tyr Trp
1               5

<210> SEQ ID NO 9
<211> LENGTH: 8
<212> TYPE: PRT
<213> ORGANISM: Mus musculus

<400> SEQUENCE: 9

Ile Asp Pro Tyr Asp Ser Glu Thr
1               5

<210> SEQ ID NO 10
<211> LENGTH: 12
<212> TYPE: PRT
<213> ORGANISM: Mus musculus

<400> SEQUENCE: 10

Val Arg Gly Gly Ser Thr Val Ala Tyr Phe Gly Val
1               5                   10

<210> SEQ ID NO 11
<211> LENGTH: 21
<212> TYPE: DNA
<213> ORGANISM: Homo sapiens

<400> SEQUENCE: 11
ctcgagcgac ctccaccaag g                                              21

```
<210> SEQ ID NO 12
<211> LENGTH: 23
<212> TYPE: DNA
<213> ORGANISM: Homo sapiens

<400> SEQUENCE: 12
tctagactcg gagagggaca gag                                              23

<210> SEQ ID NO 13
<211> LENGTH: 26
<212> TYPE: DNA
<213> ORGANISM: Homo sapiens

<400> SEQUENCE: 13
ctgcagatca cgcgaactgt ggctgc                                           26

<210> SEQ ID NO 14
<211> LENGTH: 37
<212> TYPE: DNA
<213> ORGANISM: Homo sapiens

<400> SEQUENCE: 14
ggcgcgcccg aagttgtccc ctctcacaat catcatc                               37

<210> SEQ ID NO 15
<211> LENGTH: 23
<212> TYPE: DNA
<213> ORGANISM: Mus musculus

<400> SEQUENCE: 15
ggtaaggggt taacagtagc agg                                              23

<210> SEQ ID NO 16
<211> LENGTH: 23
<212> TYPE: DNA
<213> ORGANISM: Mus musculus

<400> SEQUENCE: 16
ctttggcctc tctgggatag aag                                              23

<210> SEQ ID NO 17
<211> LENGTH: 24
<212> TYPE: DNA
<213> ORGANISM: Mus musculus

<400> SEQUENCE: 17
cacgatgata atatggccac aacc                                             24

<210> SEQ ID NO 18
<211> LENGTH: 23
<212> TYPE: DNA
<213> ORGANISM: Mus musculus

<400> SEQUENCE: 18
caccggttgg gggaagtagt act                                              23

<210> SEQ ID NO 19
<211> LENGTH: 566
<212> TYPE: PRT
<213> ORGANISM: Influenza A virus

<400> SEQUENCE: 19
```

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Ala Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
    370                 375                 380

Glu Ser Thr Gln Lys Ala Ile Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
```

```
                420                 425                 430
Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
        450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Ile Arg Asn Gly Thr Tyr Asn Pro Gln Tyr Ser Glu Glu Ala Arg Leu
                500                 505                 510

Lys Arg Glu Glu Ile Ser Gly Val Lys Leu Glu Ser Ile Gly Thr Tyr
            515                 520                 525

Gln Ile Leu Ser Ile Tyr Ser Thr Val Ala Ser Ser Leu Ala Leu Ala
        530                 535                 540

Ile Met Ile Ala Gly Leu Ser Leu Trp Met Cys Ser Asn Gly Ser Leu
545                 550                 555                 560

Gln Cys Arg Ile Cys Ile
                565

<210> SEQ ID NO 20
<211> LENGTH: 550
<212> TYPE: PRT
<213> ORGANISM: Influenza A virus

<400> SEQUENCE: 20

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220
```

```
Arg Met Glu Phe Phe Trp Ala Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
            245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
                340                 345                 350

Gly Tyr His His Ser Asn Glu Gln Gly Ser Gly Tyr Ala Ala Asp Lys
            355                 360                 365

Glu Ser Thr Gln Lys Ala Ile Gly Val Thr Asn Lys Val Asn Ser Ile
370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
            435                 440                 445

Asp Lys Val Arg Leu Gln Leu Arg Asp Asn Ala Lys Glu Leu Gly Asn
    450                 455                 460

Gly Cys Phe Glu Phe Tyr His Lys Cys Asp Asn Glu Cys Met Glu Ser
465                 470                 475                 480

Ile Arg Asn Gly Thr Tyr Asn Pro Gln Tyr Ser Glu Glu Ala Arg Leu
                485                 490                 495

Lys Arg Glu Glu Ile Ser Gly Val Lys Leu Glu Ser Ile Gly Thr Tyr
            500                 505                 510

Gln Ile Leu Ser Ile Tyr Ser Thr Val Ala Ser Ser Leu Ala Leu Ala
            515                 520                 525

Ile Met Ile Ala Gly Leu Ser Leu Trp Met Cys Ser Asn Gly Ser Leu
    530                 535                 540

Gln Cys Arg Ile Cys Ile
545                 550

<210> SEQ ID NO 21
<211> LENGTH: 341
<212> TYPE: DNA
<213> ORGANISM: Homo sapiens
<220> FEATURE:
<221> NAME/KEY: CDS
<222> LOCATION: (3)..(341)

<400> SEQUENCE: 21 ac tgg ggc cag ggc acc ctg gtc atc gtc tcc tca gcc tcc acc aag      47
   Trp Gly Gln Gly Thr Leu Val Ile Val Ser Ser Ala Ser Thr Lys
   1               5                   10                  15 ggc cca tcg gtc ttc ccc ctg gca ccc tcc tcc aag agc acc tct ggg     95
```

```
Gly Pro Ser Val Phe Pro Leu Ala Pro Ser Ser Lys Ser Thr Ser Gly
             20                  25                  30 ggc aca gcg gcc ctg ggc tgc ctg gtc aag gac tac ttc ccc gaa ccg      143
Gly Thr Ala Ala Leu Gly Cys Leu Val Lys Asp Tyr Phe Pro Glu Pro
             35                  40                  45 gtg acg gtg tcg tgg aac tca ggc gcc ctg acc agc ggc gtg cac acc      191
Val Thr Val Ser Trp Asn Ser Gly Ala Leu Thr Ser Gly Val His Thr
         50                  55                  60 ttc ccg gct gtc cta cag tcc tca gga ctc tac tcc ctc agc agc gtg      239
Phe Pro Ala Val Leu Gln Ser Ser Gly Leu Tyr Ser Leu Ser Ser Val
     65                  70                  75 gtg acc gtg ccc tcc agc agc ttg ggc acc cag acc tac atc tgc aac      287
Val Thr Val Pro Ser Ser Ser Leu Gly Thr Gln Thr Tyr Ile Cys Asn
 80                  85                  90                  95 gtg aat cac aag ccc agc aac acc aag gtg gac aag aaa gtt gag ccc      335
Val Asn His Lys Pro Ser Asn Thr Lys Val Asp Lys Lys Val Glu Pro
                100                 105                 110 aaa tct                                                              341
Lys Ser <210> SEQ ID NO 22
<211> LENGTH: 113
<212> TYPE: PRT
<213> ORGANISM: Homo sapiens

<400> SEQUENCE: 22

Trp Gly Gln Gly Thr Leu Val Ile Val Ser Ser Ala Ser Thr Lys Gly
1               5                  10                  15

Pro Ser Val Phe Pro Leu Ala Pro Ser Ser Lys Ser Thr Ser Gly Gly
             20                  25                  30

Thr Ala Ala Leu Gly Cys Leu Val Lys Asp Tyr Phe Pro Glu Pro Val
         35                  40                  45

Thr Val Ser Trp Asn Ser Gly Ala Leu Thr Ser Gly Val His Thr Phe
     50                  55                  60

Pro Ala Val Leu Gln Ser Ser Gly Leu Tyr Ser Leu Ser Ser Val Val
 65                  70                  75                  80

Thr Val Pro Ser Ser Ser Leu Gly Thr Gln Thr Tyr Ile Cys Asn Val
                 85                  90                  95

Asn His Lys Pro Ser Asn Thr Lys Val Asp Lys Lys Val Glu Pro Lys
            100                 105                 110

Ser

<210> SEQ ID NO 23
<211> LENGTH: 1209
<212> TYPE: DNA
<213> ORGANISM: Homo sapiens
<220> FEATURE:
<221> NAME/KEY: CDS
<222> LOCATION: (336)..(656)

<400> SEQUENCE: 23
ttctaaactc tgagggggtc ggatgacgtg gccattcttt gcctaaagca ttgagtttac      60
tgcaaggtca gaaaagcatg caaagccctc agaatggctg caaagagctc aacaaaaca     120 atttagaact ttattaagga ataggggaa gctaggaaga aactcaaaac atcaagattt     180
taaatacgct tcttggtctc cttgctataa ttatctggga taagcatgct gttttctgtc     240
tgtccctaac atgccctgtg attatccgca acaacacac ccaggggcag aactttgtta     300
cttaaacacc atcctgtttg cttctttcct cagga act gtg gct gca cca tct     353
```

```
                        Thr Val Ala Ala Pro Ser
                         1               5 gtc ttc atc ttc ccg cca tct gat gag cag ttg aaa tct gga act gcc      401
Val Phe Ile Phe Pro Pro Ser Asp Glu Gln Leu Lys Ser Gly Thr Ala
             10                  15                  20 tct gtt gtg tgc ctg ctg aat aac ttc tat ccc aga gag gcc aaa gta      449
Ser Val Val Cys Leu Leu Asn Asn Phe Tyr Pro Arg Glu Ala Lys Val
             25                  30                  35 cag tgg aag gtg gat aac gcc ctc caa tcg ggt aac tcc cag gag agt      497
Gln Trp Lys Val Asp Asn Ala Leu Gln Ser Gly Asn Ser Gln Glu Ser
         40                  45                  50 gtc aca gag cag gac agc aag gac agc acc tac agc ctc agc agc acc      545
Val Thr Glu Gln Asp Ser Lys Asp Ser Thr Tyr Ser Leu Ser Ser Thr
 55                  60                  65                  70 ctg acg ctg agc aaa gca gac tac gag aaa cac aaa gtc tac gcc tgc      593
Leu Thr Leu Ser Lys Ala Asp Tyr Glu Lys His Lys Val Tyr Ala Cys
                 75                  80                  85 gaa gtc acc cat cag ggc ctg agc tcg ccc gtc aca aag agc ttc aac      641
Glu Val Thr His Gln Gly Leu Ser Ser Pro Val Thr Lys Ser Phe Asn
             90                  95                 100 agg gga gag tgt tag agggagaagt gccccacct gctcctcagt tccagcctga       696
Arg Gly Glu Cys
            105 cccctccca tcctttggcc tctgacccct tttccacagg ggacctaccc ctattgcggt     756
cctccagctc atctttcacc tcacccccct cctcctcctt ggctttaatt atgctaatgt    816
tggaggagaa tgaataaata aagtgaatct ttgcacctgt ggtttctctc tttcctcaat    876
ttaataatta ttatctgttg tttaccaact actcaatttc tcttataagg gactaaatat    936
gtagtcatcc taaggcgcat aaccatttat aaaaatcatc cttcattcta ttttacccta    996
tcatcctctg caagacagtc ctccctcaaa cccacaagcc ttctgtcctc acagtcccct    1056
gggccgtggt aggagagact tgcttccttg ttttcccctc ctcagcaagc cctcatagtc    1116 cttttttaagg gtgacaggtc ttacggtcat atatcctttg attcaattcc ctgggaatca   1176
accaaggcaa attttcaaa agaagaaacc tgc                                  1209

<210> SEQ ID NO 24
<211> LENGTH: 106
<212> TYPE: PRT
<213> ORGANISM: Homo sapiens

<400> SEQUENCE: 24

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

MONOCLONAL ANTIBODY SPECIFIC TO MAJOR NEUTRALIZING EPITOPE OF INFLUENZA H5 HEMAGGLUTININ

CROSS-REFERENCE OF THE RELATED APPLICATION

The present application is a 35 U.S.C. §371 National Phase Entry Application of PCT/SG2010/000306, filed 23 Aug. 2010, and designating the United States, which is incorporated herein by reference.

SEQUENCE SUBMISSION

The present application is being filed along with a Sequence Listing in electronic format. The Sequence Listing is entitled 2577_203_Sequence_Listing.txt, created on 20 Aug. 2010. The information in the electronic format of the Sequence Listing is incorporated herein by reference in its entirety.

BACKGROUND OF THE INVENTION

The present invention relates to the murine monoclonal antibody 4C2 or to chimeric or humanized monoclonal antibodies specific to a major neutralizing epitope of influenza H5 hemagglutinin and active fragments thereof. The present invention also relates to methods and compositions for the prophylaxis and treatment of H5N1 influenza using such murine or chimeric or humanized monoclonal antibodies or fragments thereof.

The publications and other materials used herein to illuminate the background of the invention or provide additional details respecting the practice, are incorporated by reference, and for convenience are respectively grouped in the Bibliography.

The recent emergence of H5N1 strains of influenza A virus and the high mortality caused by them in humans has raised concerns for the possibility of a future influenza pandemic. Preventive and therapeutic measures against circulating H5N1 strains have received a lot of interest and effort globally to prevent another pandemic outbreak. Present vaccine strategies have been hindered by antigenic variation of the influenza strains. Present vaccine strategies requiring endogenous synthesis of antibodies will not provide immediate protection against H5N1 infections in the event of a pandemic. Currently licensed antiviral drugs include the M2 ion-channel inhibitors (rimantidine and amantidine) and the neuraminidase inhibitors (oseltamivir and zanamivir). The H5N1 viruses are known to be resistant to the M2 ion-channel inhibitors (Beigel et al., 2005). Newer strains of H5N1 viruses are being isolated which are also resistant to the neuraminidase inhibitors i.e oseltamivir and zanamivir (Le et al., 2005, de Jong and Hien, 2006). The neuraminidase inhibitors also require high doses and prolonged treatment (de Jong and Hien, 2006), increasing the likelihood of unwanted side effects. Hence, alternative strategies for treatment of influenza are warranted.

Passive immunotherapy using monoclonal antibodies (mAbs) has been viewed as a viable option for treatment of many infectious diseases. Currently, there has been a lot of focus on therapeutic approaches using neutralizing antibodies against the HA1 protein of the influenza virus. This protein is easy to target as it is on the surface of the virus and antibodies against this protein can neutralize the virus efficiently. Hence, monoclonal antibodies against neutralizing epitopes of H5 hemagglutinin (HA) may be an attractive alternative to active vaccination of humans, in particular for those individuals who are at high risk from influenza infection, viz. the immunocompromised patients, infants, young children or the elderly who do not respond well to active immunization. Passive immunization by transfusion of human convalescent sera was associated with 50% reduction in mortality during an influenza pandemic and was shown to be effective against H5N1 influenza A viral infection (Kong and Zhou, 2004; Luke et al., 2006). It is important that any mAb product should offer broad protection against circulating strains of H5N1 influenza and should prevent the selection of neutralization escape mutants in vivo.

SUMMARY OF THE INVENTION

The present invention relates to monoclonal antibodies specific to a major neutralizing epitope of influenza H5 hemagglutinin and active fragments thereof. The present invention also relates to methods and compositions for the prophylaxis and treatment of H5N1 influenza using such monoclonal antibodies or fragments thereof.

Thus, in a first aspect, the present invention provides monoclonal antibodies specific to a major neutralizing epitope of influenza H5 hemagglutinin and active fragments thereof, i.e., antigen binding fragments (also referred to herein as antibody fragments). In one embodiment, the monoclonal antibody is murine monoclonal antibody 4C2. In a second embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody 4C2 specifically binds. In one embodiment, a monoclonal antibody (either a murine monoclonal antibody or a chimeric or humanized monoclonal antibody) or fragment thereof specifically binds to a conformational epitope of H5 hemagglutinin (HA), wherein the conformational epitope is comprised of amino acids 155 (Ser) and 189 (Mg) of the mature HA protein. In another embodiment, the complimentarity determining regions (CDRs) of the light chain variable region (LCDRs) are located within the amino acid sequence set forth in SEQ ID NO:2 (also referred to herein as HM448828 which is the amino acid sequence of the mouse light chain variable region). In an additional embodiment, the amino acid sequences for the light chain variable CDRs are: LCDR1: QDISGH (SEQ ID NO:5); LCDR2: HGT (SEQ ID NO:6); and LCDR3: VQYVQFPWT (SEQ ID NO:7). In one embodiment, the complimentarity determining regions (CDRs) of the heavy chain variable region (HCDRs) are located within the amino acid sequence set forth in SEQ ID NO:4 (also referred to herein as HM448827 which is the amino acid sequence of the mouse heavy chain variable region). In another embodiment, the amino acid sequences for the heavy chain variable CDRs are: HCDR1: GYTFT-TYW (SEQ ID NO:8); HCDR2: IDPYDSET (SEQ ID NO:9); and HCDR3: VRGGSTVAYFGV (SEQ ID NO:10).

In one embodiment, the DNA encoding HM448828 comprises the nucleotide sequence set forth in SEQ ID NO:1. In another embodiment, the DNA encoding HM448827 comprises the nucleotide sequence set forth in SEQ ID NO:3. In one embodiment, the light chain variable region comprises the amino acid sequence set forth in SEQ ID NO:2. In another embodiment, the heavy chain variable region comprises the amino acid sequence set forth in SEQ ID NO:4. In one embodiment, the heavy and light constant regions are obtained from human antibody-producing cells by standard cloning techniques. In another embodiment the human heavy chain constant region is a human IgG1 heavy chain constant region. In an additional embodiment, the human IgG1 heavy chain constant region comprises the amino acid sequence set forth in SEQ ID NO:22 (GenBank Accession No. AAX09634.1). In a further embodiment, a nucleic acid sequence encoding this amino acid sequence is set forth in SEQ ID NO:21 (GenBank Accession No. AY885218.1). In one embodiment, the human light chain constant region is a human kappa light chain constant region. In another embodiment, the human kappa light chain constant region comprises the amino acid sequence set forth in SEQ ID NO:24 (GenBank Accession No. AAA58989.1). In a further embodiment, a nucleic acid encoding this sequence is set forth in SEQ ID NO:23 (GenBank Accession No. J00241.1).

In another embodiment, the present invention provides a nucleic acid encoding the murine monoclonal antibody 4C2 or the chimeric or humanized monoclonal antibodies described herein or antigen binding fragment thereof. Examples of nucleic acid sequences include those described herein. In an additional embodiment, the present invention provides a vector comprising the nucleic acid. In a further embodiment, the present invention proves a cell comprising and expressing the vector.

In a second aspect, the present invention provides methods and compositions for the prophylaxis and treatment of H5N1 influenza using such murine monoclonal antibody 4C2 or chimeric or humanized monoclonal antibodies or fragments thereof. In one embodiment, the present invention provides a pharmaceutical composition comprising the murine monoclonal antibody 4C2 or the chimeric or humanized monoclonal antibodies described herein and a pharmaceutically acceptable diluent or carrier. In another embodiment, the pharmaceutical composition comprises an antigen binding fragment of the monoclonal antibodies described herein and a pharmaceutically acceptable diluent or carrier. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H5N1 virus infection in a subject, or lowering the risk of influenza H5N1 virus infection in a subject, inhibiting infection of a subject by one or more influenza H5N1 virus strains or isolates, or prophylaxis of influenza infection or disease by one or more influenza H5N1 virus strains or isolates. In this embodiment, the method comprises administering to a subject in need thereof, a therapeutically effective amount of the murine monoclonal antibody 4C2 or the chimeric or humanized monoclonal antibodies described herein, or an antigen binding fragment thereof, a nucleic acid molecule comprising a polynucleotide encoding said antibody or antibody fragment; a vector comprising said polynucleotide; or a cell expressing said vector. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H5N1 virus infection. In a further embodiment, the agent that is administered to the subject is administered prior to, substantially contemporaneously with or following influenza H5N1 virus infection of the subject.

DETAILED DESCRIPTION OF THE INVENTION

Figure 1A:
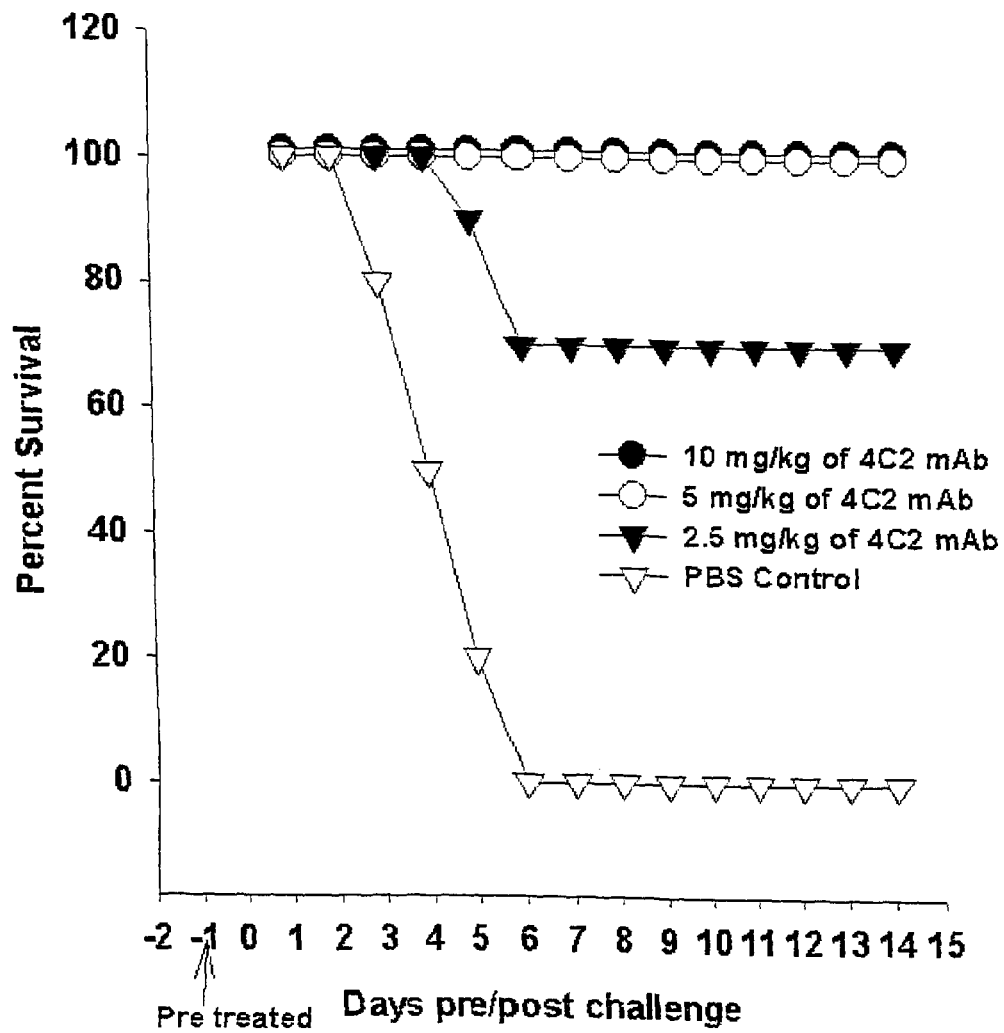
FIGS. 1A and 1B show the prophylactic efficacy of 4C2 mAb in mice. Each group of mice was pre-treated with 2.5 mg/kg, 5 mg/kg or 10 mg/kg of 4C2 mAb, one day before challenge with $5MLD_{50}$ of mouse-adapted Indonesian HPAI H5N1 from Clade 1 A/HK/213/2003 (FIG. 1A) or clade 2.1 virus A/TLL013/06 (FIG. 1B). Mice were monitored for survival throughout a 14 day observation period. The results are expressed in terms of percent survival.

The present invention relates to the murine monoclonal antibody 4C2 or to chimeric or humanized monoclonal antibodies specific to a major neutralizing epitope of influenza H5 hemagglutinin and active fragments thereof. The present invention also relates to methods and compositions for the prophylaxis and treatment of H5N1 influenza using such murine or chimeric or humanized monoclonal antibodies or fragments thereof.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e., molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to $V_H$-CH$_1$ by a disulfide bond. The F(ab')$_2$ may be reduced under mild conditions to break the disulfide linkage in the hinge region thereby converting the F(ab')$_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include chimeric or humanized monoclonal antibodies, as well as active fragments thereof. Examples of active fragments of molecules that bind to known antigens include separated light and heavy chains, Fab, Fab/c, Fv, Fab', and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw et al. (1982); Rousseaux et al. (1986).

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston et al. (1988). A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513; 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. See, e.g., U.S. Patent Application Publication No. 2010/0080800. The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al. (1988).

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al. (1998)), molecular modeling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human. Methods to obtain "humanized antibodies" are well known to those skilled in the art. See, e.g., U.S. Patent Application Publication No. 2010/0080800.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Hieter et al. (1980)) and the heavy constant chain is the human IgG4 constant chain.

The term variable region (VR) as used herein refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The term framework region (FR) as used herein refers to one or more of the framework regions within the variable regions of the light and heavy chains of an antibody (See Kabat et al. (1992); Johnson and Wu (2001); http colon backslash backslash immuno dot bme dot nwa dot edu). These expressions include those amino acid sequences regions interposed between the CDRs within the variable regions of the light and heavy chains of an antibody.

CDR and FR residues are determined according to a standard sequence definition (Kabat et al. (1992), and a structural definition (e.g., as in Chothia and Lesk (1987)). Where these two methods result in slightly different identifications of a CDR, the structural definition is preferred, but the residues identified by the sequence definition method are considered important FR residues for determining which framework residues to import into a consensus sequence.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding). Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis.

Further, the term "therapeutically effective amount" refers to the amount of antibody which, when administered to a human or animal, which is sufficient to result in a therapeutic effect in said human or animal. The effective amount is readily determined by one of skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

In a first aspect, the present invention provides monoclonal antibodies specific to a major neutralizing epitope of influenza H5 hemagglutinin and active fragments thereof, i.e., antigen binding fragments (also referred to herein as antibody fragments). In one embodiment, the monoclonal antibody is murine monoclonal antibody 4C2. Murine monoclonal antibody 4C2 is produced by mouse hybridoma 4C2. Mouse hybridoma 4C2 was deposited on 3 Aug. 2010 under terms of the Budapest Treaty with the American Type Culture Collection, 10801 University Blvd., Manassas, Va. 20110, USA, and assigned Accession Number PTA-11241. The present invention also pertains to the hybridoma producing the murine monoclonal antibody 4C2. In a second embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody 4C2 specifically binds. In one embodiment, a monoclonal antibody (either a murine monoclonal antibody or a chimeric or humanized monoclonal antibody) or fragment thereof specifically binds to a conformational epitope of H5 hemagglutinin (HA), wherein the conformational epitope is comprised of amino acids 155 (Ser) and 189 (Arg) of the mature HA protein. In another embodiment, the complimentarity determining regions (CDRs) of the light chain variable region (LCDRs) are located within the amino acid sequence set forth in SEQ ID NO:2 (also referred to herein as HM448828 which is the amino acid sequence of the mouse light chain variable region). In an additional embodiment, the amino acid sequences for the light chain variable CDRs are: LCDR1: QDISGH (SEQ ID NO:5); LCDR2: HGT (SEQ ID NO:6); and LCDR3: VQYVQFPWT (SEQ ID NO:7). In one embodiment, the complimentarity determining regions (CDRs) of the heavy chain variable region (HCDRs) are located within the amino acid sequence set forth in SEQ ID NO:4 (also referred to herein as HM448827 which is the amino acid sequence of the mouse heavy chain variable region). In another embodiment, the amino acid sequences for the heavy chain variable CDRs are: HCDR1: GYTFTTYW (SEQ ID NO:8); HCDR2: IDPYDSET (SEQ ID NO:9); and HCDR3: VRGGSTVAYFGV (SEQ ID NO:10).

In one embodiment, the DNA encoding HM448828 comprises the nucleotide sequence set forth in SEQ ID NO:1. In another embodiment, the DNA encoding HM448827 comprises the nucleotide sequence set forth in SEQ ID NO:3. In one embodiment, the light chain variable region comprises the amino acid sequence set forth in SEQ ID NO:2. In another embodiment, the heavy chain variable region comprises the amino acid sequence set forth in SEQ ID NO:4. In one embodiment, the heavy and light constant regions are human. In another embodiment the human heavy chain constant region is a human IgG1 heavy chain constant region. In an additional embodiment, the human IgG1 heavy chain constant region comprises the amino acid sequence set forth in SEQ ID NO:22 (GenBank Accession No. AAX09634.1). In a further embodiment, a nucleic acid sequence encoding this amino acid sequence is set forth in SEQ ID NO:21 (GenBank Accession No. AY885218.1). In one embodiment, the human light chain constant region is a human kappa light chain constant region. In another embodiment, the human kappa light chain constant region comprises the amino acid sequence set forth in SEQ ID NO:24 (GenBank Accession No. AAA58989.1). In a further embodiment, a nucleic acid encoding this sequence is set forth in SEQ ID NO:23 (GenBank Accession No. J00241.1).

In another embodiment, the present invention provides a nucleic acid encoding the murine monoclonal antibody 4C2 or chimeric or humanized monoclonal antibodies described herein or antigen binding fragment thereof. Examples of nucleic acid sequences include those described herein. In an additional embodiment, the present invention provides a vector comprising the nucleic acid. In a further embodiment, the present invention proves a cell comprising and expressing the vector.

In one embodiment, humanized antibodies are prepared by combining human heavy and light chain constant regions with the mouse heavy and light chain variable regions using techniques described herein, as well as techniques well known to the skilled artisan. In another embodiment, humanized antibodies are prepared in which DNA sequences are synthesized which encode for humanized $V_L$ and $V_H$ sequences which contain the CDRs of the mouse light and heavy light chain variable regions described herein, respectively.

Methods for synthesizing DNA encoding for a protein of known sequence are well known in the art. Using such methods, DNA sequences which encode the subject humanized antibodies of the present invention are synthesized, and then expressed in vector systems suitable for expression of recombinant antibodies. This may be effected in any vector system which provides for the subject humanized antibody sequences of the present invention, such as expression of fusion proteins comprising the human constant domain sequences and the mouse variable domain sequences which are associated to produce functional (antigen binding) antibodies.

Expression vectors, host cells suitable for expression of recombinant antibodies and humanized antibodies in particular and methods suitable for expression of such antibodies are well known in the art. See, e.g., U.S. Pat. No. 7,074,406.

Host cells known to be capable of expressing functional immunoglobulins include by way of example mammalian cells such as Chinese Hamster Ovary (CHO) cells, COS cells, myeloma cells, bacteria such as *Escherichia coli*, yeast cells such as *Saccharomyces cerevisiae*, among other host cells. Of these, CHO cells are used by many researchers given their ability to effectively express and secrete immunoglobulins.

Essentially, recombinant expression of humanized antibodies is effected by one of two general methods. In the first method, the host cells are transfected with a single vector which provides for the expression of both heavy and light variable sequences fused to selected constant regions. In the second method, host cells are transfected with two vectors, which respectively provide for expression of either the variable heavy or light sequence fused to selected constant regions.

In a second aspect, the present invention provides methods and compositions for the prophylaxis and treatment of H5N1 influenza using such murine monoclonal antibody 4C2 or chimeric or humanized monoclonal antibodies or fragments thereof. In one embodiment, the present invention provides a pharmaceutical composition comprising the murine monoclonal antibody 4C2 or the chimeric or humanized monoclonal antibodies described herein and a pharmaceutically acceptable diluent or carrier. In another embodiment, the pharmaceutical composition comprises an antigen binding fragment of the monoclonal antibodies described herein and a pharmaceutically acceptable diluent or carrier. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H5N1 virus infection in a subject, or lowering the risk of influenza H5N1 virus infection in a subject, inhibiting infection of a subject by one or more influenza H5N1 virus strains or isolates, or prophylaxis of influenza infection or disease by one or more influenza H5N1 virus strains or isolates. In this embodiment, the method comprises administering to a subject in need thereof, a therapeutically effective amount of the murine monoclonal antibody 4C2 or the chimeric or humanized monoclonal antibodies described herein, or an antigen binding fragment thereof, a nucleic acid molecule comprising a polynucleotide encoding said antibody or antibody fragment; a vector comprising said polynucleotide; or a cell expressing said vector. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H5N1 virus infection. In a further embodiment, the agent that is administered to the subject is administered prior to, substantially contemporaneously with or following influenza H5N1 virus infection of the subject.

The antibodies according to the invention can be prepared in a physiologically acceptable formulation and may comprise a pharmaceutically acceptable carrier, diluent and/or excipient using known techniques. For example, the antibody according to the invention and as described herein including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art. See, e.g., *Remington: The Science and Practice of Pharmacy,* 21st Ed., Ed. D. B. Troy, Lippincott, Williams & Wilkins, Baltimore, 2006, hereby incorporated by reference herein.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), .alpha.-secretase activators, .beta.- and .gamma.-secretase inhibitors, tau proteins, neurotransmitter, .beta.-sheet breakers, attractants for amyloid beta clearing/depleting cellular components, inhibitors of N-terminal truncated amyloid beta including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, *Ginkgo biloba*, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, eg intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on the intended use.

In the present invention, a panel of monoclonal antibodies (mAbs) against HA2 gp was characterized for their respective epitopes by epitope mapping. The therapeutic and prophylactic efficacies of these mAbs were evaluated in mice challenged with HPAI H5N1 virus infection. The prophylactic and therapeutic efficacy of one of these mAbs was evaluated against two highly pathogenic H5N1 virus strains from clades 1 and 2.1 in a murine model. Efficacy was determined by observation of weight loss, survival and kinetics of viral load clearance in the lungs of the infected mice. Chimeric or humanized mAbs were prepared from this mAb.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Viruses: H5N1 human influenza viruses from clade 2.1 A/Indonesia/CDC669/2006, A/Indonesia/TLL012/2006, A/Indonesia/TLL013/2006, A/Indonesia/TLL014/2006 and A/Indonesia/CDC326/2006 were obtained from the Ministry of Health (MOH), Indonesia. *** The viruses from different clades (clade 0-A/Hongkong/156/97, clade 1.0-A/Hong Kong/213/2004, clade 4.0-A/goose/Guiyang/337/06 and clade 8.0-A/chicken/Henan/12/04) were rescued by Reverse Genetics (RG) (WHO, 2005). Briefly, the synthesized HA and NA genes were cloned into a dual-promoter plasmid for influenza A reverse genetics. Dual-promoter plasmids were obtained from Center for Disease Control and Prevention, Atlanta, Ga., USA. The reassortant virus was rescued by transfecting plasmids containing HA and NA together with the remaining six gene plasmids derived from A/Puerto Rico/8/34 (H1N1) into co-culture of 293T and MDCK cells using Lipofectamine 2000 (Invitrogen Corp. USA). Stock viruses were propagated in the allantoic cavities of 11-day-old embryonated chicken eggs at 35° C. for 36 91 h. All experiments with highly pathogenic viruses were conducted in a BSL 3+ containment facility in compliance with CDC/NIH and WHO recommendations and also were approved by the Agri-Food and Veterinary Agency and MOH, Singapore.

MAb production: BALB/c mice were immunized twice subcutaneously at regular intervals of 2 weeks with inactivated whole virus from A/Indonesia/TLL014/2006 in 0.1 ml of Phosphate Buffered Saline (PBS), which was emulsified with an equal volume of adjuvant Montanide ISA563 (SEPPIC, France). Mice were boosted with the same viral antigen, 3 days before the fusion of splenocytes with SP2/0 cells. The fused cells were seeded in 96-well plates, and their supernatants were screened by immunofluorescence assays as described below. The hybridomas that produced the mAbs were cloned by limiting dilution at least three times. The positive mAbs were tested for their hemagglutination inhibition activity as described below. Immunoglobulins from selected positive mAbs were isotyped using a commercial isotyping kit (Amersham Bioscience, England) as described in the manufacturer's protocol. The mAbs were purified using Protein A sepharose beads (Millipore). Purity of the antibodies was confirmed by SDS-PAGE analysis. The mAbs were then tested for neutralization activity by standard hemagglutination inhibition assay as described below.

Immunofluorescence assay (IFA): MDCK cells cultured in 96-well plates were infected with AIV H5N1 strains. At 24-48 h post-infection, the cells were fixed with 4% paraformaldehyde for 30 min at room temperature and washed thrice with phosphate buffered saline (PBS), pH 7.4. Fixed cells were incubated with hybridoma culture supernatant at 37° C. for 1 h, rinsed with phosphate buffered saline (PBS) and then incubated with a 1:40 dilution of fluorescein isothiocyanate (FITC)-conjugated rabbit anti-mouse Immunoglobulin (Dako, Denmark). Cells were rinsed again in PBS and antibody binding was evaluated by wide-field epi-fluorescence microscopy (Olympus IX71).

Hemagglutination inhibition assay: Hemagglutination inhibition (HI) assays were performed as described previously (Webster et al., 1991). Briefly, mAbs were serially diluted (2 fold) in V-bottom 96-well plates and mixed with 4 HA units of virus H5N1 viruses. Plates were incubated for 30 min at room temperature, and 1% chicken RBCs were added to each well. The hemagglutination inhibition endpoint was the highest mAb dilution in which agglutination was not observed.

Isolation and analysis of escape mutants: The epitope recognized by mAb 4C2 was mapped by characterization of escape mutants as described previously (Kaverin et al., 2007). Briefly, H5N1 viruses were incubated with an excess of mAb for 1 h and then inoculated into 11 day old embryonated chicken eggs. For isolation of in vivo escape mutants, the lung samples from the treated mice were inoculated directly into the embryonated eggs. The eggs were incubated at 37° C. for 48 h. Virus was harvested and used for cloning in limiting dilution in embryonated chicken eggs and the escape mutants were plaque purified. RNA was extracted from the allantoic fluid. The hemagglutinin gene was reverse transcriptase (RT)-PCR amplified and cloned into a TA-cloning vector (Promega) and several clones were sequenced. The sequences of individual clones were analyzed by comparison with the sequences of the parent virus.

Cloning of chimeric IgG1 expression plasmid: Design of the expression vector was as described (Jostock et al., 2004). Briefly, human antibody constant regions encoding the kappa light chain and the IgG1 heavy chain were amplified using the following primers: human IgG1 constant heavy chain: forward primer 5'-CTCGAGCGACCTCCACCAAGG-3' (SEQ ID NO:11) and reverse primer 5'-TCTAGACTCGGAGAGG-GACAGAG-3' (SEQ ID NO:12); human constant kappa light chain: forward primer 5'-CTGCAGATCACGCGAACT-GTGGCT GC-3' (SEQ ID NO:13) and reverse primer 5'-GGCGCGCCCGAAGTTGTCCCCTCTCACAA TCATC ATC-3' (SEQ ID NO:14). The amplified constant regions of the kappa light chain and the IgG1 heavy chain were cloned into a modified pCMV/myc/ER plasmid with an internal ribosome entry site (IRES) of encephalomyocarditis virus inserted in between them. Unique restriction sites were introduced to allow for insertion of the variable regions of the heavy and light chains in frame with the constant regions. mRNA was prepared from the mAb 4C2 hybridoma cells and used in first strand cDNA synthesis with random hexamers. The total cDNA was used as template to amplify both the variable heavy and light chain using the primers and protocols of the mouse scFv recombinant antibody phage system (Amersham Biosciences). The resultant products were cloned into pCR-Script (Stratagene, USA) for sequencing. Sequence-specific primers were then designed as follows: 4C2 specific variable light chain: forward primer 5'-GG TAAGGGGT-TAACAGTAGCAGG-3' (SEQ ID NO:15) and reverse primer 5'-CTTTGGCCTC TCTGGGATAGAAG-3' (SEQ ID NO:16); 4C2 specific variable heavy chain: forward primer 5'-CACGATGATAATATGGCCACAACC-3' (SEQ ID NO:17) and reverse primer 5'-CACCG GTTGGGGGAAG-TAGTACT-3' (SEQ ID NO:18). These primers were used for amplification of the variable regions, which were then cloned into the expression vector. The 4C2 specific variable light chain coding sequence is set forth in SEQ ID NO:3 and the 4C2 specific variable heavy chain coding sequence is set forth in SEQ ID NO:1. Expression of this construct leads to the production of chimeric antibodies containing 33% of the sequences as mouse variable regions from murine and 67% of the sequences as human constant regions for IgG1.

Transient expression of chimeric antibodies and purification: Chimeric antibodies were expressed using the Freestyle 293 expression system (Invitrogen, USA) to obtain antibodies produced in a defined, serum-free medium. The above mentioned construct was transfected into 293-F cells using 293fectin (Invitrogen, USA) and supernatants were collected 120 h after transfection. The chimeric antibody 4C2 (ch-mAb 4C2 or ch4C2) was purified using Protein A sepharose beads (Millipore). Purity of the chimeric antibodies were confirmed by SDS-PAGE and immunoblot analysis using HRP labeled antihuman Ig (DAKO) was used to confirm introduction of human constant regions.

Microneutralization assay: Neutralization activity of the monoclonal antibodies against H5N1 strains was analyzed by microneutralization assay as previously described (Prabakaran et al., 2008). Briefly, ten times diluted mAb was further serially diluted (two-fold) and incubated with 100 50% tissue culture infectious doses (TCID50) of different clades of H5N1 strains for 1 h at room temperature and plated in duplicate onto MDCK cells grown in a 96-well plate. The TCID50 of each of the H5N1 strains in MDCK cell culture was determined by the Reed and Muench method. The neutralizing titer was assessed as the highest mAb dilution in which no cytopathic effect was observed by light microscopy.

Challenge study: Inbred SPF BALB/c mice aged 4-6 weeks were used for the challenge studies. Mice (n=10 per group) were intranasally infected with 5MLD50 (Mouse lethal dose 50%) of two different H5N1 strains (RG-A/Hongkong/213/2003 from clade 1 and A/Indonesia/TLL013/06 from clade 2.1). All animal experiments were carried out in accordance with the Guides for Animal Experiments Performed at NIID and experimental protocols.

Prophylactic efficacy: To determine the prophylactic efficacy, mice were pre-treated intraperitoneally with 2.5 mg/kg, 5 mg/kg, 10 mg/kg or 0 mg/kg (PBS) of monoclonal antibody (4C2 or ch4C2), prior to the viral challenge. After 24 h, mice were challenged with 5MLD50 of the two different H5N1 strains. Mice were observed daily to monitor body weight and mortality until all animals died or until day 14 after challenge.

Therapeutic efficacy. To determine the therapeutic efficacy of the chimeric mAb group of mice was challenged with 5MLD50 of the two different H5N1 strains. 24 h after viral challenge, the mice were treated via intra-peritoneal route with 2.5 mg/kg, 5 mg/kg, 10 mg/kg or 0 mg/kg (PBS) of monoclonal antibody (4C2 or ch4C2). Mice were observed daily to monitor body weight and mortality until all animals died or until day 14 after challenge.

Example 2

Characterization and Chimerization of Murine mAb 4C2

A panel of mAbs against influenza hemagglutinin (HA) was screened for efficient neutralization of different strains of H5N1 viruses. The amino acids involved in forming the epitopes of the 4C2 mAb were analyzed using selection of neutralization escape mutants. The amino acid sequence of the HA protein including signal protein is set forth in SEQ ID NO:19, and the amino acid sequence of the mature HA protein is set forth in SEQ ID NO:20. Sequencing of the complete HA gene isolated from multiple escape variants to 4C2 mAb carried single point mutations at amino acid positions 155 (Ser to Ile) and 189 (Arg to Lys) (with respect to the mature HA protein set forth in SEQ ID NO:20). The mAb 4C2 was chosen for therapeutic studies in the mouse model based on its reactivity with the H5N1 viruses and high HI activity (Table 1) and neutralizing titers (Table 2).

TABLE 1

Hemagglutination Inhibition Titers of 4C2 mAb Against Different Clades of H5N1 Strains

| Virus strain | H5N1 Virus clades | HI titer |
| --- | --- | --- |
| A/Indonesia/TLL014 | Clade 2.1 | 512 |
| A/Indonesia/TLL013 | Clade 2.1 | 512 |
| A/Indonesia/CDC669/06 | Clade 2.1 | 512 |
| A/Hongkong/156/97 | Clade 0 | 256 |
| A/goose/Guiyang/337/06 | Clade 4 | 256 |
| A/chicken/Henan/12/04 | Clade 8 | 512 |
| RG-A/Hong Kong/213/2004 | Clade 1 | 256 |
| A/chicken/Singapore/Sg02 H3N2 | — | <4 |
| A/Common iora/Indonesia/F89/H7N1 | — | <4 |

The hemagglutination inhibition titers of the murine mAb 4C2 (1 mg/ml) were measured with different viruses.

TABLE 2

Micro-neutralization Titers of 4C2 mAb Against Different Clades of H5N1 Strains

| Virus strain | H5N1 Virus clades | Microneutralization titers against H5N1 strains# |
| --- | --- | --- |
| A/Indonesia/TLL014 | Clade 2.1 | 320 |
| A/Indonesia/TLL013 | Clade 2.1 | 640 |
| A/Indonesia/CDC669/06 | Clade 2.1 | 320 |
| A/Hongkong/156/97 | Clade 0 | 320 |
| A/goose/Guiyang/337/06 | Clade 4 | 320 |
| A/chicken/Henan/12/04 | Clade 8 | 640 |
| RG-A/Hong Kong/213/2004 | Clade 1 | 320 |
| A/chicken/Singapore/Sg02 H3N2 | — | <10 |
| A/Common iora/Indonesia/F89/H7N1 | — | <10 |

Virus microneutralization of the mAb 4C2 (1 mg/ml) were measured with different clades of H5N1 viruses.
*Concentration of each n-mAb at 1 mg/ml
100TCID50 of each virus strain used for microneutralization assay Example 3

Prophylactic Treatment with 4C2 mAb Protects Mice from Lethal Viral Challenge

Figure 1B:
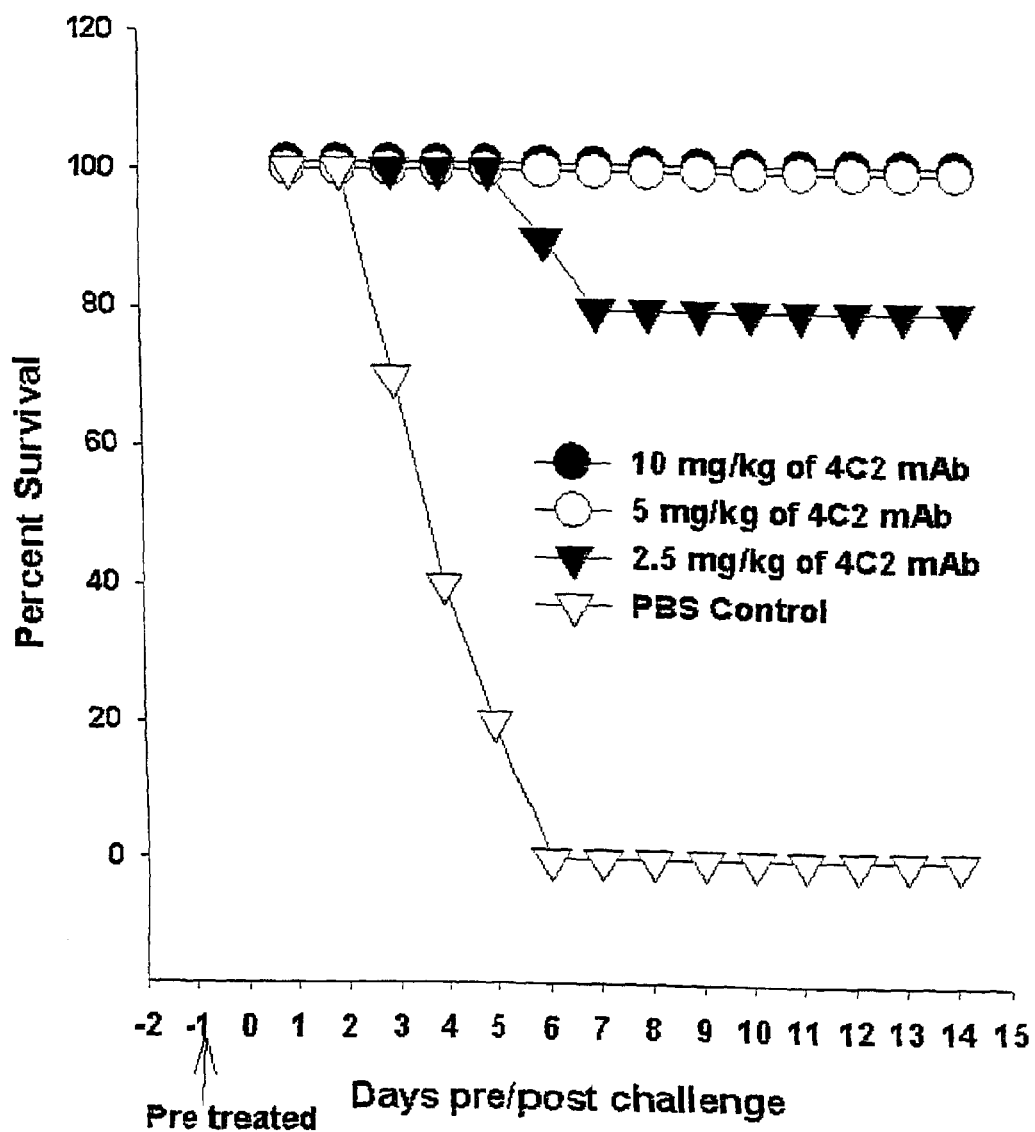

We examined the protective efficacy of 4C2 mAb in mice challenged with clade 1 or clade 2.1 strains of H5N1 virus. All mice pre-treated with a single dose of 5 mg/kg or 10 mg/kg of 4C2 were protected from death following the lethal challenge with 5MLD50 of both clades of H5N1 viruses (100% protection) (FIG. 1A, 1B), whereas all untreated control mice died from viral infection by day 6 after challenge. Moreover, mice pre-treated with even lowest concentration of 2.5 kg/mg of 4C2 showed protection of 70 and 80% against clade 1 (FIG. 1A) and clade 2.1 (FIG. 1B) and virus challenge respectively.

Example 4

Therapeutic Treatment with 4C2 Protects Mice from Lethal Viral Challenge

Figure 2A:
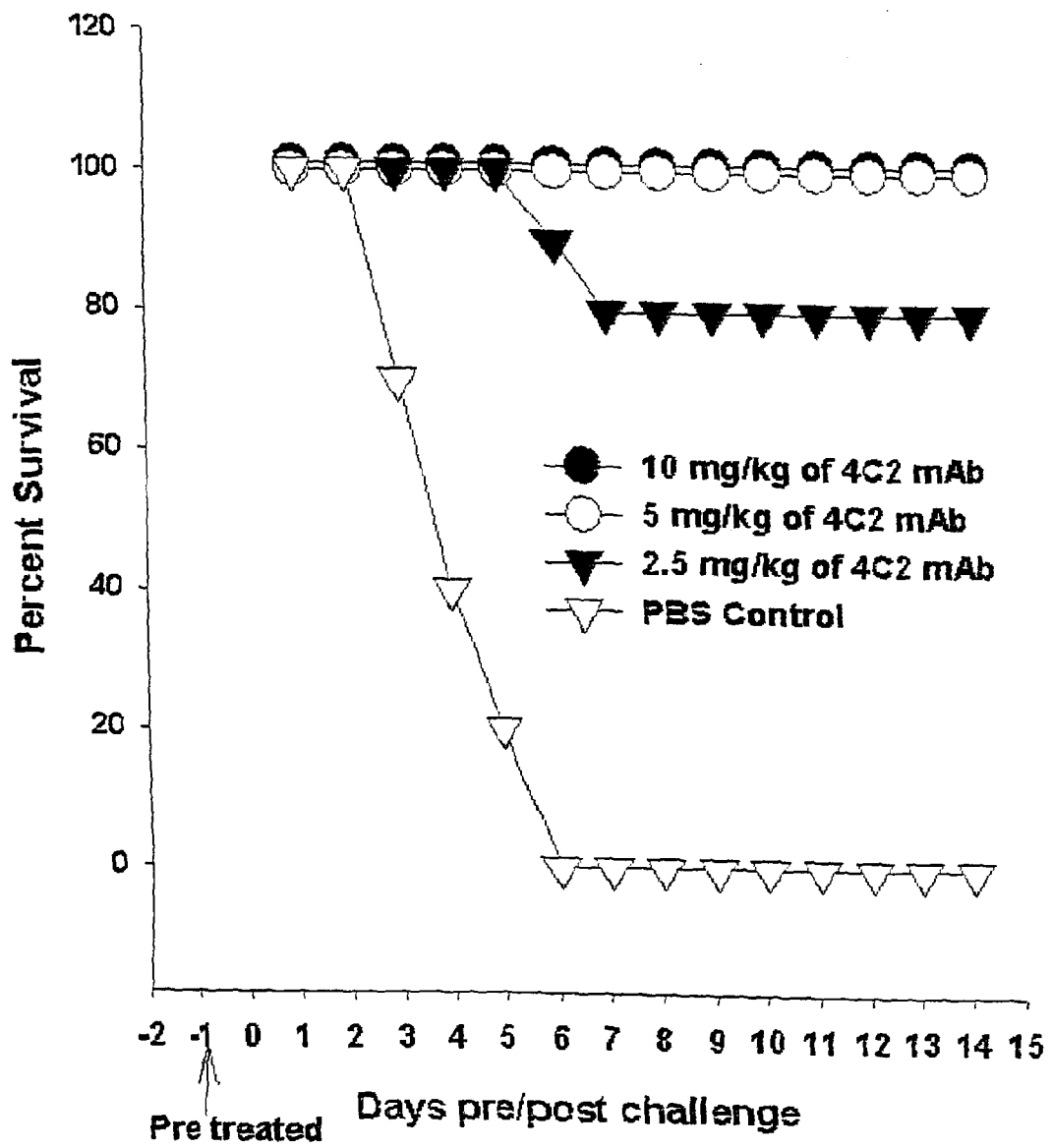
FIGS. 2A and 2B show the therapeutic efficacy of 4C2 mAb in mice. Each group of mice was treated with 2.5 mg/kg, 5 mg/kg or 10 mg/kg of 4C2 mAb one day after challenge with mouse-adapted Indonesian HPAI H5N1 from Clade 1 A/HK/213/2003 (FIG. 2A) and clade 2.1 virus A/TLL013/06 (FIG. 2B) Mice were monitored for survival throughout a 14 day observation period. The results are expressed in terms of percent survival.
Figure 2B:
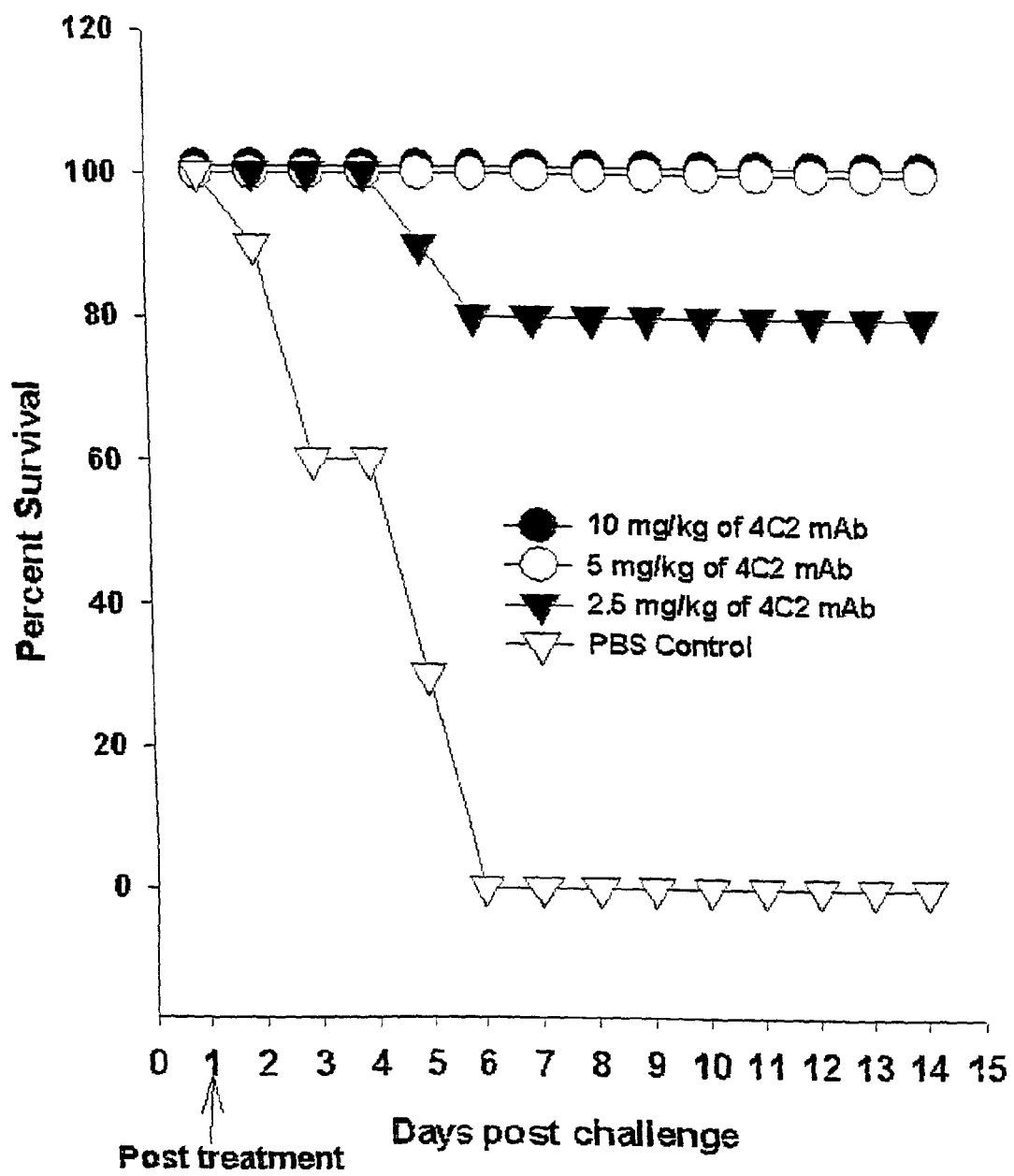

To determine the therapeutic efficacy of 4C2 mAb against H5N1 lethal challenge, mice were challenged with 5MLD50 of clade 1 or clade 2.1 virus strains. Twenty four hours after viral challenge, the mice were treated with 2.5 mg, 5 mg/kg or 10 mg/kg of 4C2. MAb 4C2 was able to protect 100% of mice from both clades of viruses at concentrations of 5 mg/kg and 10 mg/kg (FIGS. 2A and 2B). Even at 2.5 mg/kg it could protect 80% of mice against lethal challenge with clade 1 and clade 2.1 viruses.

Example 5

Chimerization of Murine mAb 4C2

Chimeric monoclonal antibodies (ch-mAbs) were generated for the mAbs such that the constant regions were replaced with those from human origin but variable regions remained from murine origin. The chimeric mAbs generated in this way were 66.6% humanized. The chimeric antibodies still retained the original properties of the murine mAbs (results not shown). In this manner, a chimeric or humanized mAb was prepared.

Example 6

Prophylactic Treatment with ch4C2 Protects Mice from Lethal Viral Challenge

Figure 3A:
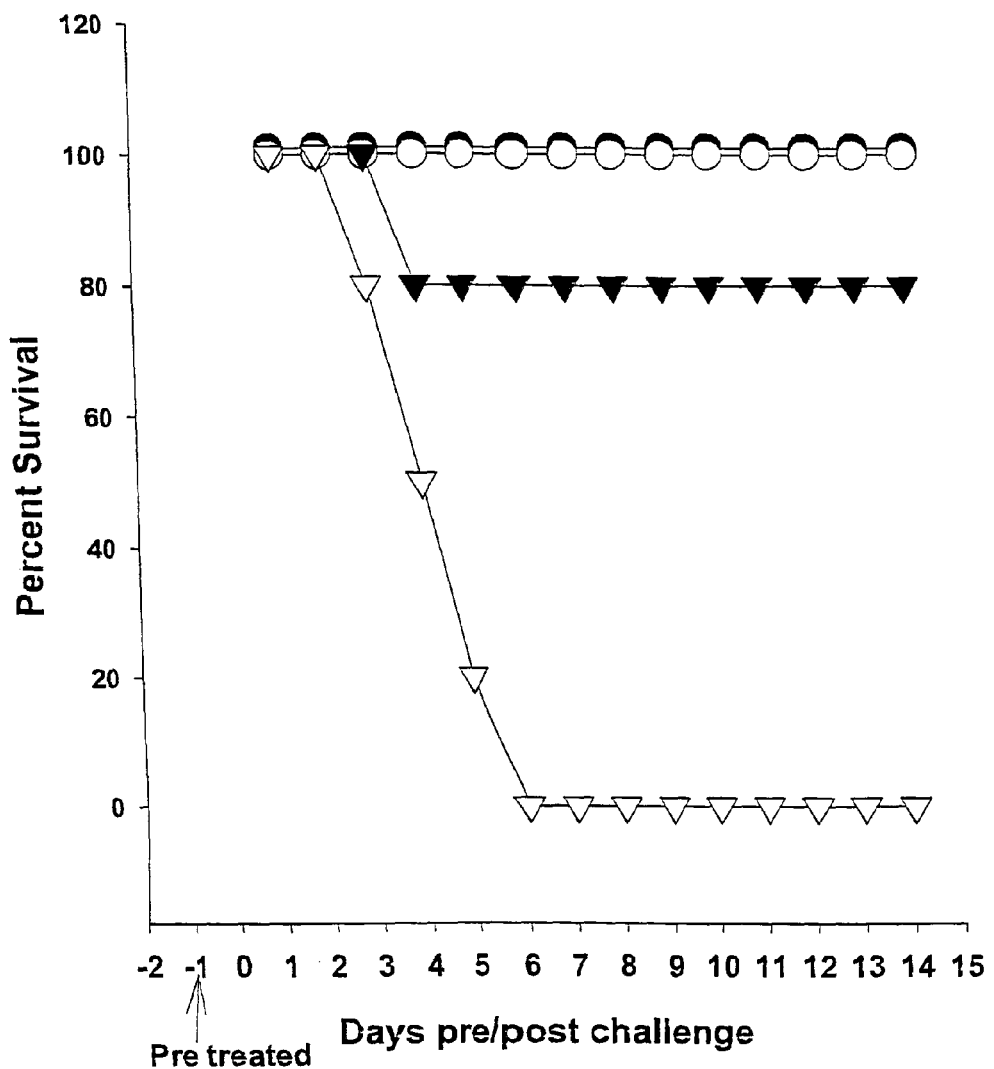
FIGS. 3A and 3B show the prophylactic efficacy of chimeric 4C2 in mice. Each group of mice was pre-treated with 2.5 mg/kg, 5 mg/kg or 10 mg/kg of ch4C2 one day before challenge with $5MLD_{50}$ of mouse-adapted Indonesian HPAI H5N1 from clade 1 A/HK/213/2003 (FIG. 3A) or clade 2.1 virus A/TLL013/06 (FIG. 3B). Mice were monitored for survival throughout a 14 day observation period. The results are expressed in terms of percent survival.
Figure 3B:
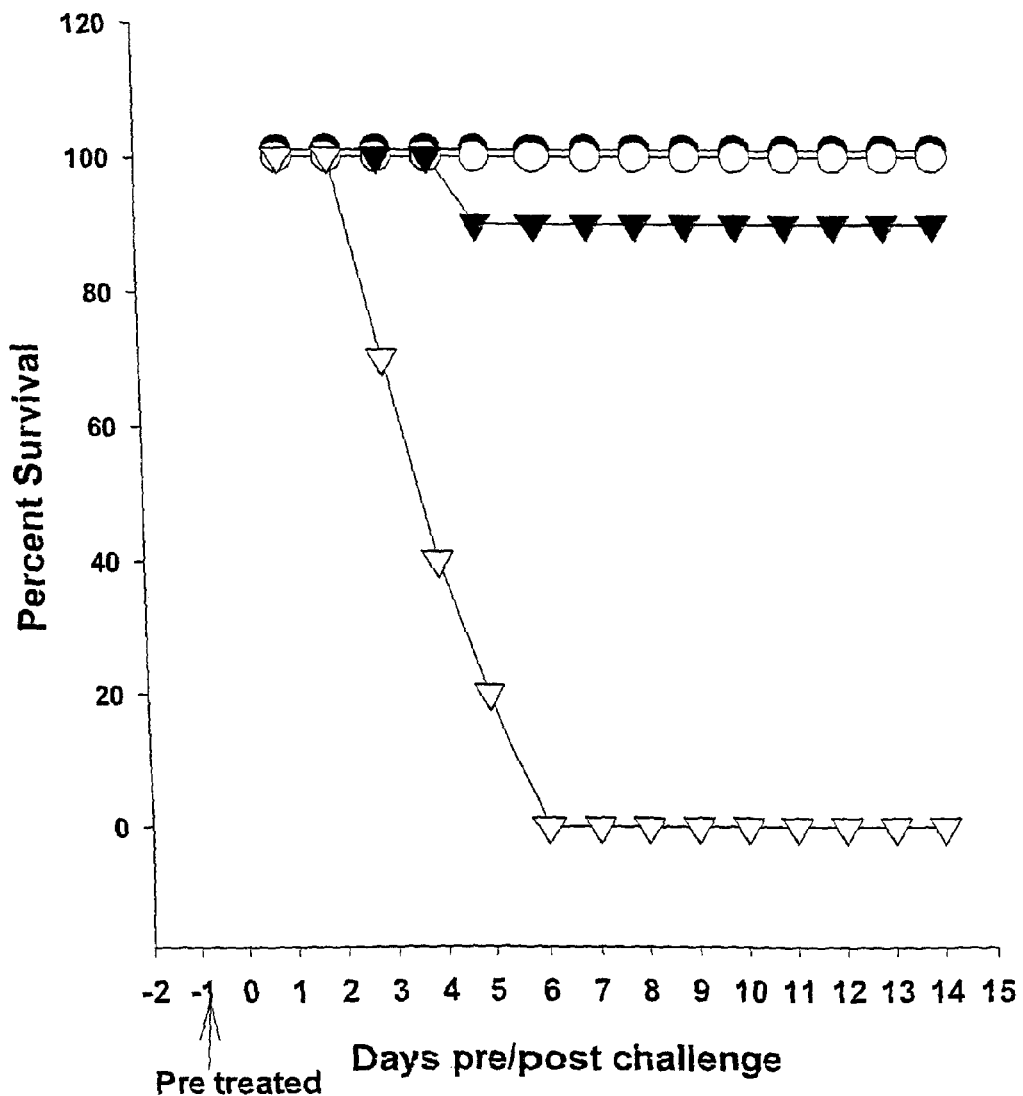

We examined the protective efficacy of ch4C2 in mice challenged with clade 1 or clade 2.1 strains of H5N1 virus. All mice pre-treated with a single dose of 5 mg/kg or 10 mg/kg of ch4C2 were protected from death following the lethal challenge with 5MLD50 of both clades of H5N1 viruses (100% protection) (FIG. 3A, 3B), whereas all untreated control mice died from viral infection by day 6 after challenge. Moreover, mice pre-treated with even lowest concentration of 2.5 kg/mg of ch4C2 showed protection of 80 and 90% against clade 1 (FIG. 3A) and clade 2.1 (FIG. 3B) and virus challenge respectively.

Example 7

Therapeutic Treatment with ch4C2 Protects Mice from Lethal Viral Challenge

Figure 4A:
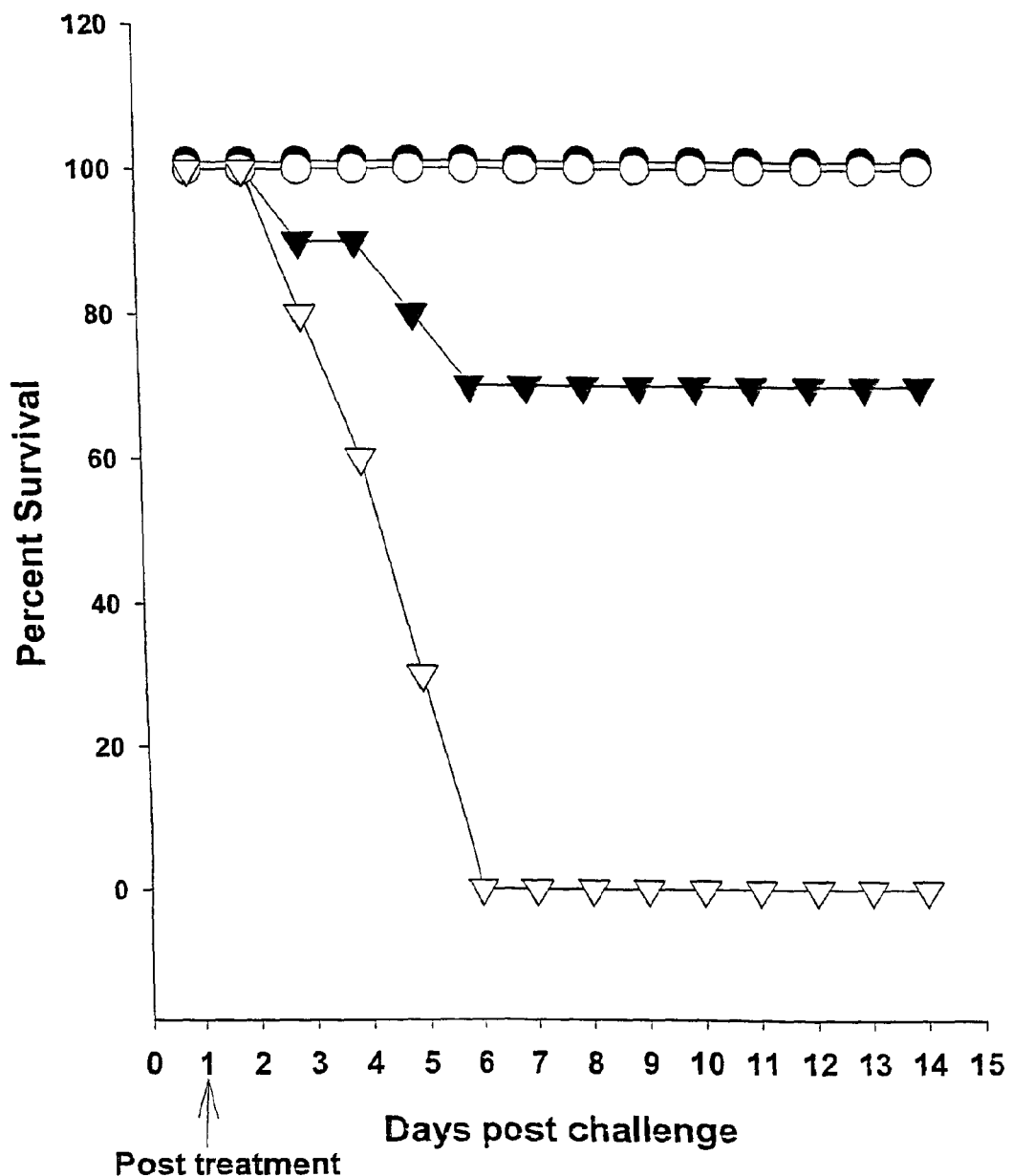
FIGS. 4A and 4B show the therapeutic efficacy of chimeric 4C2 in mice. Each group of mice was treated with 2.5 mg/kg, 5 mg/kg or 10 mg/kg of ch4C2 one day after challenge with mouse-adapted Indonesian HPAI H5N1 from clade 1 A/HK/213/2003 (FIG. 4A) and clade 2.1 virus A/TLL013/06 (FIG. 4B) Mice were monitored for survival throughout a 14 day observation period. The results are expressed in terms of percent survival.
Figure 4B:
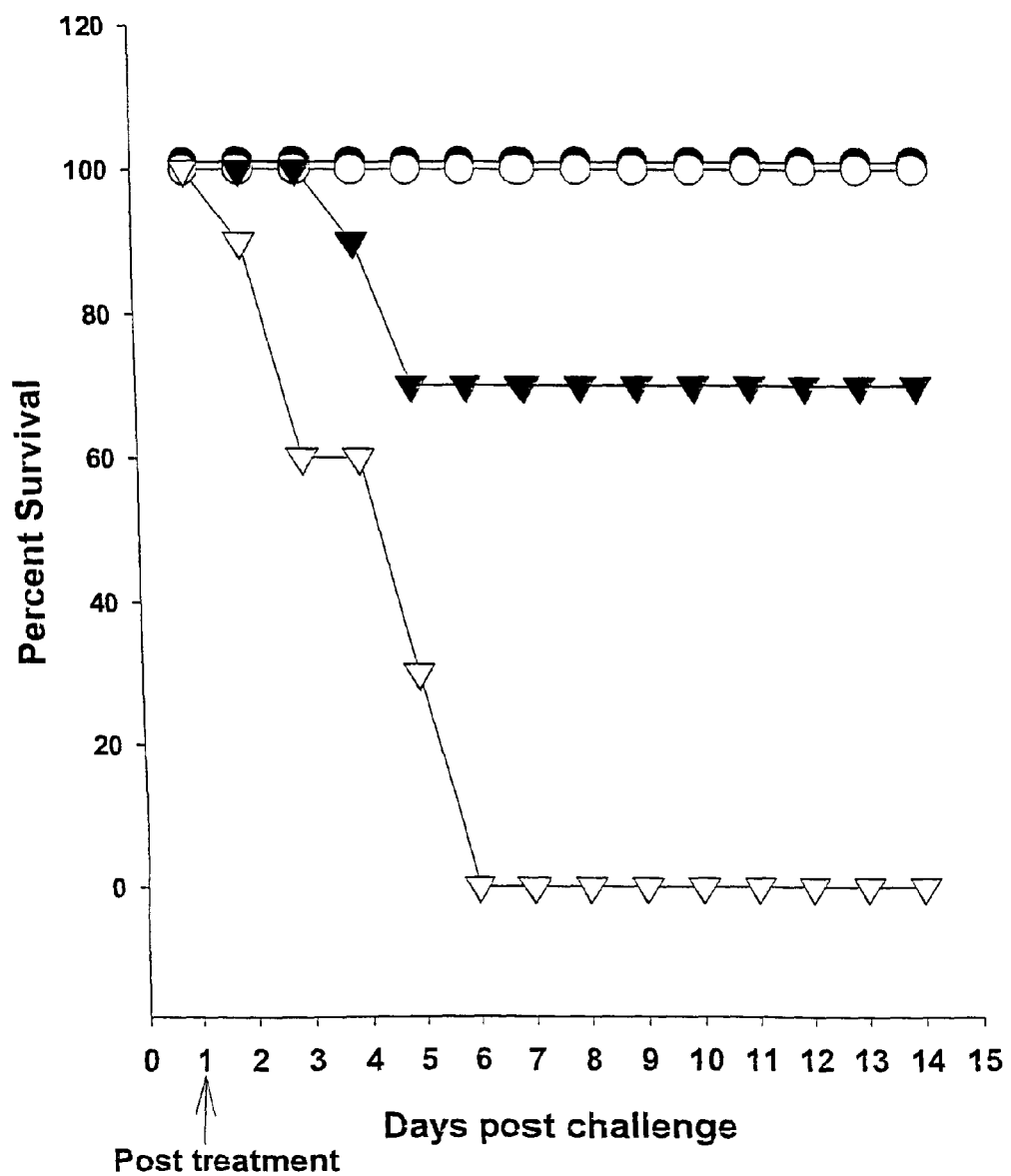

To determine the therapeutic efficacy of ch4C2 against H5N1 lethal challenge, mice were challenged with 5MLD50 of clade 1 or clade 2.1 virus strains. Twenty four hours after viral challenge, the mice were treated with 2.5 mg, 5 mg/kg or 10 mg/kg of ch4C2. Ch4C2 was able to protect 100% of mice from both clades of viruses at concentrations of 5 mg/kg and 10 mg/kg (FIGS. 4A and 4B). Even at 2.5 mg/kg it could protect 70% of mice from lethal challenge with clade 1 and clade 2.1 viruses.

Epitope mapping using escape mutant analysis demonstrated that Ser155 and Arg189 are the major determinants of the epitope of mAb 4C2. Also, the presence of the amino acid of the epitope in the highly antigenic 150's loop and 189 amino acid positions explains its high neutralizing capacity. Therefore, in the present study we selected murine antibody 4C2 for the prophylactic and therapeutic study against lethal H5N1 infections. In addition, we selected this antibody for chimerization and the subsequent use of the chimeric antibody in a prophylactic and therapeutic study against lethal H5N1 infections. Moreover, passive administration of antibodies remains a strategy which can be explored against pandemic influenza. The prophylactic or therapeutic administration of either 4C2 mAb or ch4C2 in a single dose showed 100% protection against lethal H5N1 influenza in a mouse model. We observed 100% protection against clades 1 and 2.1 of H5N1 viruses using 10 m/kg and 5 mg/kg of 4C2 or ch4C2. A dose of 5 mg/kg provided sufficient protection and effected virus elimination in 9 days after viral challenge, though a dose of 10 mg/kg eliminated the virus in only 6 days after viral challenge. Therapy with 4C2 or ch4C2 probably helped to control the initial course of infection, thus allowing the animal to mount an effective immune response. Our studies suggest that use of passive immunotherapy using mAb 4C2 or chimeric mAb ch4C2 can be an effective tool in both the prophylaxis and treatment of highly pathogenic H5N1 infection, providing the immediate immunity needed to contain a future influenza pandemic. The chimeric antibodies produced herein can be further humanized by grafting of the complementary determining regions using techniques well known in the art. The chimeric antibodies can be pre-clinically evaluated in sub-human primates. The effectiveness of a single dose for both prophylaxis and treatment in the mouse studies implies that the efficacy of the antibody may still be maintained even if the chimeric antibody does illicit an immune response itself.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Chothia C and Lesk A M (1987). Canonical structures for the hypervariable regions of immunoglobulins. *J Mol Biol* 196:901-917.

de Jong M D, Hien T T (2006). Avian influenza A (H5N1)-Review. *J Clin Virol* 35: 2-13.

Hieter P A, Max E E, Seidman J G, Maizel J V Jr, Leder P (1980). Cloned human and mouse kappa immunoglobulin constant and J region genes conserve homology in functional segments. Cell 22:197-207.

Huston J S, Levinson D, Mudgett-Hunter M, Tai M S, Novotný J, Margolies M N, Ridge R J, Bruccoleri R E, Haber E, Crea R, et al. (1988). Protein engineering of antibody binding sites: recovery of specific activity in an anti-digoxin single-chain Fv analogue produced in *Escherichia coli*. *Proc Nat Acad Sci USA* 85:5879-5883.

Johnson, G and Wu, T T (2001). Kabat Database and its applications: future directions. *Nucleic Acids Research* 29:205-206.

Jostock T, Vanhove M, Brepoels E, van Gool R, Daukandt M, et al. (2004) Rapid generation of functional human IgG antibodies derived from Fab-onphage display libraries. *J Immunol Methods* 289: 65-80.

Kabat E A, Wu T T, Perry H M, Gottesman K S, Foeller C (1992). *Sequences of Proteins of Immunological Interest*, U.S. Department of Health and Human Services.

Kaverin N V, Rudneva I A, Ilyushina N A, Varich N L, Lipatov A S, et al. (2007). Structure of antigenic sites on the hemagglutinin molecule of H5 influenza virus and phenotypic variation of escape mutants. *J Gen Virol* 83: 2497-2505.

Khaw B A, Strauss H W, Carvalho A, Locke E, Gold H K, Haber E (1982). Technetium-99m labeling of antibodies to cardiac myosin Fab and to human fibrinogen. *J Nucl Med* 23:1011-1019.

Kong L K, Zhou B P. (2006). Successful treatment of avian influenza with convalescent plasma. *Hong Kong Med J* 357: 489.

Le Q M, Kiso M, Someya K, Sakai Y T, Nguyen T H, et al. (2005). Avian flu: Isolation of drug-resistant H5N1 virus. *Nature* 437: 1108.

Luke T C, Kilbane E M, Jackson J L, Hoffman S L. (2006). Meta-analysis: Convalescent blood products for Spanish Influenza Pneumonia: A future H5N1 treatment? *Ann Intern Med* 145:599-609.

Prabakaran M, Velumani S, He F, Karuppannan A K, Geng G Y, et al. (2008) Protective immunity against influenza H5N1 virus challenge in mice by intranasal co-administration of baculovirus surface-displayed HA and recombinant CTB as an adjuvant. *Virology* 380:412-420.

Rader C, Cheresh D A, Barbas C F $3^{rd}$ (1998). A phage display approach for rapid antibody humanization: designed combinatorial V gene libraries. *Proc Natl Acad Sci USA* 95:8910-8915.

Riechmann L, Clark M, Waldmann H, Winter G (1988). Reshaping human antibodies for therapy. *Nature* 332:323-327.

Rousseaux J, Rousseaux-Prevost R, Bazin H (1986). Optimal conditions for the preparation of proteolytic fragments from monoclonal IgG of different rat IgG subclasses. *Methods Enzymology* 121:663-69, Academic Press.

Webster R G, Kawaoka Y, Taylor J, Weinberg R, Paoletti E (1991). Efficacy of nucleoprotein and hemagglutinin antigens expressed in fowlpox virus as vaccine for influenza in chickens. *Vaccine* 9:303-308.

WHO. Evolution of H5N1 avian influenza viruses in Asia. *Emerg Infect Dis* 2005; 11:395 1515-1521.

The invention claimed is:

1. A monoclonal antibody or antibody fragment which specifically binds to a conformational epitope of H5 hemagglutinin, wherein the conformational epitope of H5 hemagglutinin is one to which murine monoclonal antibody 4C2 as produced by hybridoma 4C2 which is deposited with the American Type Culture Collection with Accession Number PTA-11241 specifically binds, wherein the conformational epitope is comprised of amino acid 155 (Ser) and amino acid 189 (Arg) of mature H5 hemagglutinin, and wherein the complementarity determining regions of the light chain variable region (LCDRs) are within the amino acid sequence set forth in SEQ ID NO:2 and the complementarity determining regions of the heavy chain variable region (HCDRs) are within the amino acid sequence set forth in SEQ ID NO:4.

2. A monoclonal antibody 4C2 as produced by hybridoma 4C2 which is deposited with the American Type Culture Collection with Accession Number PTA-11241.

3. The monoclonal antibody or antibody fragment of claim 1, wherein the monoclonal antibody or fragment thereof is a chimeric or humanized monoclonal antibody.

4. The monoclonal antibody or antibody fragment of claim 1, wherein the H5 hemagglutinin comprises the amino acid sequence set forth in SEQ ID NO:20.

5. The monoclonal antibody of claim 1, wherein the complementarity determining regions are: LCDR1: QDISGH (SEQ ID NO:5); LCDR2: HGT (SEQ ID NO:6); LCDR3: VQYVQFPWT (SEQ ID NO:7); HCDR1: GYTFTTYW (SEQ ID NO:8); HCDR2: IDPYDSET (SEQ ID NO:9); and HCDR3: VRGGSTVAYFGV (SEQ ID NO:10).

6. The monoclonal antibody or antibody fragment of claim 1, wherein the light chain variable region comprises the amino acid sequence set forth in SEQ ID NO:2.

7. The monoclonal antibody or antibody fragment of claim 1, wherein the heavy chain variable region comprises the amino acid sequence set forth in SEQ ID NO:4.

8. The monoclonal antibody or antibody fragment of claim 1, wherein the light chain variable region comprises the amino acid sequence set forth in SEQ ID NO:2 and the heavy chain variable region comprises the amino acid sequence set forth in SEQ ID NO:4.

9. A nucleic acid encoding the monoclonal antibody or antibody fragment of claim 1.

10. A vector comprising the nucleic acid of claim 9.

11. An isolated host cell comprising and expressing the vector of claim 10.

12. A pharmaceutical composition comprising an agent and a pharmaceutically acceptable diluent or carrier, wherein the agent is selected from the group consisting of (a) the monoclonal antibody or antibody fragment of claim 1, (b) a nucleic acid molecule comprising a nucleic acid encoding said monoclonal antibody or antibody fragment, (c) a vector comprising said nucleic acid and (d) a cell expressing said vector.

13. A method of reducing influenza H5N1 virus infection in a subject, or lowering the risk of influenza H5N1 virus infection in a subject, or inhibiting infection of a subject by one or more influenza H5N1 virus strains or isolates, or prophylaxis of influenza infection or disease by one or more influenza H5N1 virus strains or isolates which comprises administering to a subject in need thereof, a therapeutically effective amount of an agent selected from the group consisting of (a) the monoclonal antibody or antibody fragment of claim 1, (b) a nucleic acid molecule comprising a nucleic acid encoding said monoclonal antibody or antibody fragment, (c) a vector comprising said nucleic acid and (d) a cell expressing said vector.

14. The method of claim 13, wherein the subject is immunocompromised, an infant, a young child or elderly.

15. The method of claim 13, wherein the administration provides a therapeutic benefit.

16. The method of claim 15, wherein the therapeutic benefit comprises (a) inhibiting increases in influenza virus titer, (b) decreasing influenza virus titer, (c) inhibiting increases in influenza virus replication, (d) decreasing influenza virus replication, (e) inhibiting increases in influenza virus proliferation or decreasing influenza virus proliferation, (f) decreasing progression, severity, frequency, duration or probability one or more symptoms or complications associated with influenza virus infection in a subject or (g) hastening a subject's recovery from influenza virus infection.

17. The method of claim 16, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

18. A pharmaceutical composition comprising the monoclonal antibody of claim 2 or antibody fragment thereof which specifically binds to the same epitope and a pharmaceutically acceptable excipient.

19. A method of reducing influenza H5N1 virus infection in a subject, or lowering the risk of influenza H5N1 virus infection in a subject, or inhibiting infection of a subject by one or more influenza H5N1 virus strains or isolates, or prophylaxis of influenza infection or disease by one or more influenza H5N1 virus strains or isolates which comprises administering to a subject in need thereof, a therapeutically effective amount of the monoclonal antibody of claim 2 or antibody fragment thereof which specifically binds to the same epitope.

20. The method of claim 19, wherein the subject is immunocompromised, an infant, a young child or elderly.

21. The method of claim 19, wherein the administration provides a therapeutic benefit.

22. The method of claim 21, wherein the therapeutic benefit comprises (a) inhibiting increases in influenza virus titer, (b) decreasing influenza virus titer, (c) inhibiting increases in influenza virus replication, (d) decreasing influenza virus replication, (e) inhibiting increases in influenza virus proliferation or decreasing influenza virus proliferation, (f) decreasing progression, severity, frequency, duration or probability one or more symptoms or complications associated with influenza virus infection in a subject or (g) hastening a subject's recovery from influenza virus infection.

23. The method of claim 22, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

* * * * *